(12) United States Patent
Newton et al.

(10) Patent No.: US 9,158,917 B2
(45) Date of Patent: Oct. 13, 2015

(54) METHODS, APPARATUSES AND COMPUTER PROGRAM PRODUCTS FOR AUDITING PROTECTED HEALTH INFORMATION

(75) Inventors: Roger Newton, Charlotte, NC (US); Barbara Brank, Charlotte, NC (US); Robert Kells, New York, NY (US); Jason K. Martin, Indian Trail, NC (US)

(73) Assignee: McKesson Financial Holdings, Hamilton (BM)

( * ) Notice: Subject to any disclaimer, the term of this patent is extended or adjusted under 35 U.S.C. 154(b) by 0 days.

(21) Appl. No.: 13/436,134

(22) Filed: Mar. 30, 2012

(65) Prior Publication Data

US 2013/0262503 A1 Oct. 3, 2013

(51) Int. Cl.
*G06F 21/55* (2013.01)
*G06F 19/00* (2011.01)
*G06F 21/62* (2013.01)

(52) U.S. Cl.
CPC ............ *G06F 21/552* (2013.01); *G06F 19/322* (2013.01); *G06F 21/6227* (2013.01); *G06F 21/6245* (2013.01); *G06F 2221/2101* (2013.01)

(58) Field of Classification Search
CPC .................... G06F 17/30595; G06F 17/30289; G06F 17/30528; G06F 17/30598; G06F 17/30705
USPC ........................................................ 707/758
See application file for complete search history.

(56) References Cited

U.S. PATENT DOCUMENTS

| | | | | |
|---|---|---|---|---|
| 2009/0326980 | A1* | 12/2009 | Nolan et al. | 705/3 |
| 2010/0088232 | A1* | 4/2010 | Gale | 705/50 |
| 2012/0221535 | A1* | 8/2012 | Dubbels et al. | 707/694 |
| 2012/0226916 | A1* | 9/2012 | Hahn et al. | 713/193 |

OTHER PUBLICATIONS

Microsoft, "MSDN: Extended Events: SLQ Server," Jan. 14, 2009 to Jul. 12, 2012, Internet Archive <http://web.archive.org/web/20090114002643/http://msdn.microsoft.com/en-us/library/bb630282.aspx>, 6 pages.

* cited by examiner

*Primary Examiner* — Truong Vo
(74) *Attorney, Agent, or Firm* — Alston & Bird LLP

(57) ABSTRACT

An apparatus is provided for auditing protected health information of one or more patients. The apparatus includes at least one memory and at least one processor configured to detect a query to access information stored in a database including patient-related information. The processor is further configured to save the query in an event file. The processor is further configured to capture query-related information associated with the query and save the query-related information in the event file. The processor is further configured to determine that the query involves protected health information. The processor is further configured to transmit, in response to determining that the query involves protected health information, the query-related information to be used in a reporting table. Corresponding computer program products and methods are also provided.

20 Claims, 5 Drawing Sheets

FIG. 4

Paragon Audit Security Report

| Date Accessed | Med Rec # | Visit ID | Patient Name | User Login ID | User Name | Workstation | Application / Program | Action | Data |
|---|---|---|---|---|---|---|---|---|---|
| July 7 08:46:39 | 0000320695 | 0003168179 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0007000111 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0007000090 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0003168864 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0007000099 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0003168854 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0003167720 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0007000105 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0003168780 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0007000087 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0007000077 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:39 | 0000320695 | 0007000094 | PEARSON, KENNEDY | probbins | ROBINSON, PATRICK | AF9ZBRM1 | Clinical CareStation | Accessed | TPM300_PAT_VISIT : Patient Visit Demographic Information |
| July 7 08:46:59 | 0000320695 | 0003168780 | PEARSON, KENNEDY | probbins | ROBINSON, PATRICK | AF9ZBRM1 | Clinical CareStation | Created | TSC125_USER_TRACE : Security Audit Trace Information |
| July 7 08:47:18 | 0000320695 | 0003168780 | PEARSON, KENNEDY | NAMCKlebcv3ut | [username = ebcv3ut] not found in Paragon databa | AD31P3Q1 | Microsoft SQL Server Management Studio - Query | Accessed | TOM107_CHILD_ORDER : Order Event detail |
| July 7 08:47:31 | 0000320695 | 0003168854 | PEARSON, KENNEDY | NAMCKlebcv3ut | [username = ebcv3ut] not found in Paragon databa | AD31P3Q1 | Microsoft SQL Server Management Studio - Query | Accessed | TOM107_CHILD_ORDER : Order Event detail |
| July 7 08:48:05 | 0000320695 | 0007000094 | PEARSON, KENNEDY | probbins | ROBINSON, PATRICK | AF9ZBRM1 | Registration | Accessed | VSM040_PERSON_HDR : Person Demographic Information |
| July 7 08:48:05 | 0000320695 | 0007000090 | PEARSON, KENNEDY | probbins | ROBINSON, PATRICK | AF9ZBRM1 | Registration | Accessed | VSM040_PERSON_HDR : Person Demographic Information |
| July 7 08:48:05 | 0000320695 | 0007000111 | PEARSON, KENNEDY | probbins | ROBINSON, PATRICK | AF9ZBRM1 | Registration | Accessed | VSM040_PERSON_HDR : Person Demographic Information |

METHODS, APPARATUSES AND COMPUTER PROGRAM PRODUCTS FOR AUDITING PROTECTED HEALTH INFORMATION

TECHNOLOGICAL FIELD

Embodiments of the invention relate generally to a mechanism of managing protected health information and more particularly relate to a method, apparatus and computer program product for monitoring access to protected health information associated with patients.

BACKGROUND

At present, the American Recovery and Reinvestment Act (ARRA) requires health care systems to be able to audit access to protected health information (PHI) of patients. PHI includes any information about the health status, provision of health care, or payment for health care that can be linked to a specific individual. As such, access to protected health information of a patient such as, for example, the patient's name, birthdate, social security number, address, etc. is generally required to be audited or detected per the ARRA.

Current health care applications may include functionality for auditing access to protected health information by that particular health care application. However, the functionality is often closely tied to the application and, therefore, limited to actions taken within or using the corresponding application alone. In this regard, some items of protected health information may not be adequately audited in existing health care systems operating multiple health care applications having varied auditing capabilities.

Additionally, since existing approaches often only audit accessing of protected health information by a particular health care application in which the auditing functionality is embedded, the existing approaches may be unable to detect an instance in which a third party hacks into the health care system and accesses protected health information outside of one of these health care applications. As such, the existing solutions may be unaware that the third party accessed the protected health information.

In view of the foregoing drawbacks, it may be beneficial to provide a more efficient and reliable manner in which to audit access to protected health information.

BRIEF SUMMARY

A method, apparatus and computer program product are therefore provided that may enable the provision of an efficient and reliable mechanism for auditing access to the protected health information of one or more patients. The protected health information of the patients may be maintained by a health care system.

An example embodiment may audit access to protected health information in a health care system and may identify one or more individuals who evaluate the PHI, make changes to the PHI or otherwise access the PHI of one or more patients of a health care facility.

An example embodiment may enable provision of an audit service that provides a complete database audit solution to monitor or detect access to protected health information regardless of the application being used to access the information. Accordingly, embodiments of the present invention enable the auditing of PHI being accessed by multiple applications within a health care system, instead of merely a single application having auditing functionality embedded therein.

As such, some example embodiments may provide improvements in tracking or monitoring access to protected health information by analyzing queries of multiple applications attempting to access the protected health information from a database.

In one exemplary embodiment, a method for auditing protected health information of one or more patients is provided. The method may include detecting a query to access information stored in a database including patient-related information. The method may further include saving the query in an event file. The method may further include capturing query-related information associated with the query and saving the query-related information in the event file. The method may further include determining that the query involves protected health information. The method may further transmitting, in response to determining that the query involves protected health information, the query-related information to be used in a reporting table.

In another exemplary embodiment, an apparatus for auditing protected health information of one or more patients is provided. The apparatus may include a memory and a processor configured to cause the apparatus to detect a query to access information stored in a database including patient-related information. The processor is further configured to cause the apparatus to save the query in an event file. The processor is further configured to capture query-related information associated with the query and save the query-related information in the event file. The processor is further configured to cause the apparatus to determine that the query involves protected health information. The processor is further configured to cause the apparatus to transmit, in response to determining that the query involves protected health information, the query-related information to be used in a reporting table.

In another exemplary embodiment, a computer program product for auditing protected health information of one or more patients is provided. The computer program product includes at least one computer-readable storage medium having computer-executable program code instructions stored therein. The computer-executable program code instructions may include program code instructions configured to detect a query to access information stored in a database including patient-related information. The computer program product may further include program code instructions configured to save the query in an event file. The computer program product may further include program code instructions configured to capture query-related information associated with the query and save the query-related information in the event file. The computer program product may further include program code instructions configured to determine that the query involves protected health information. The computer program product may further include program code instructions configured to cause transmission, in response to determining that the query involves protected health information, of the query-related information to be used in a reporting table.

BRIEF DESCRIPTION OF THE SEVERAL VIEWS OF THE DRAWINGS

Figure 1:
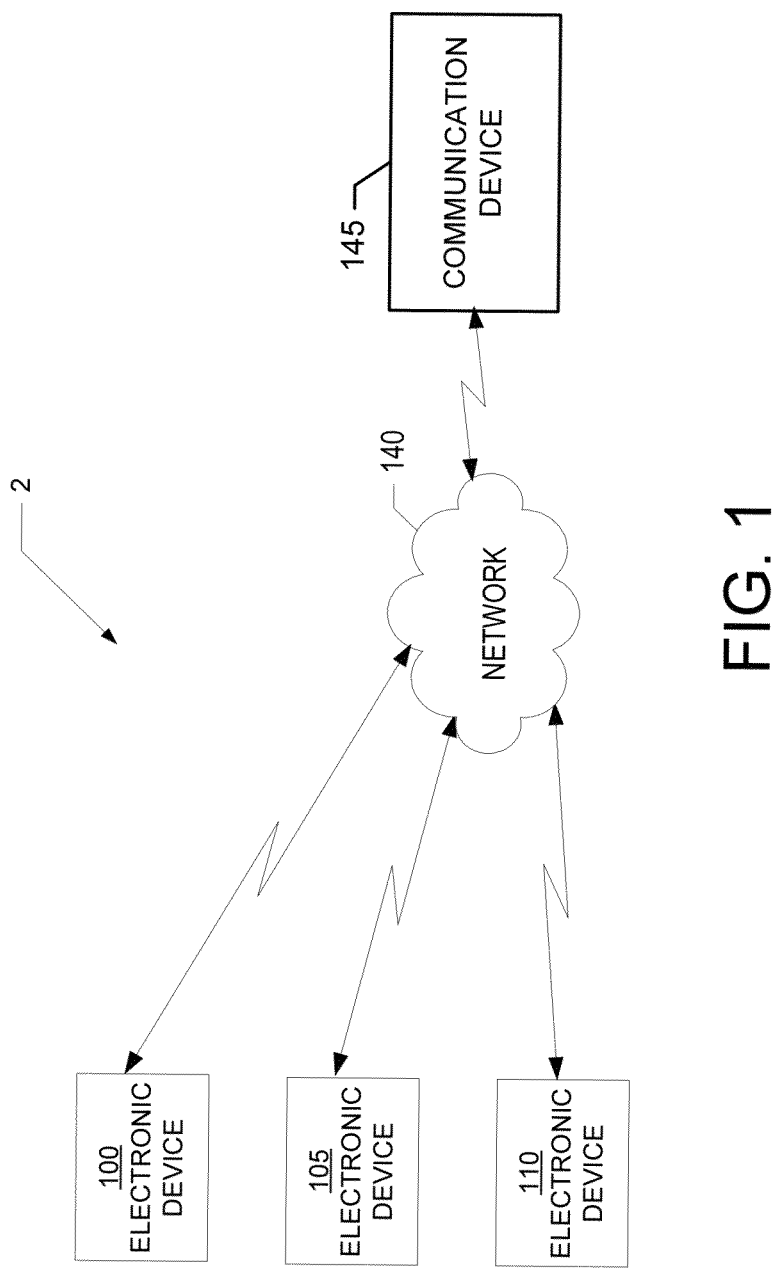
Figure 2:
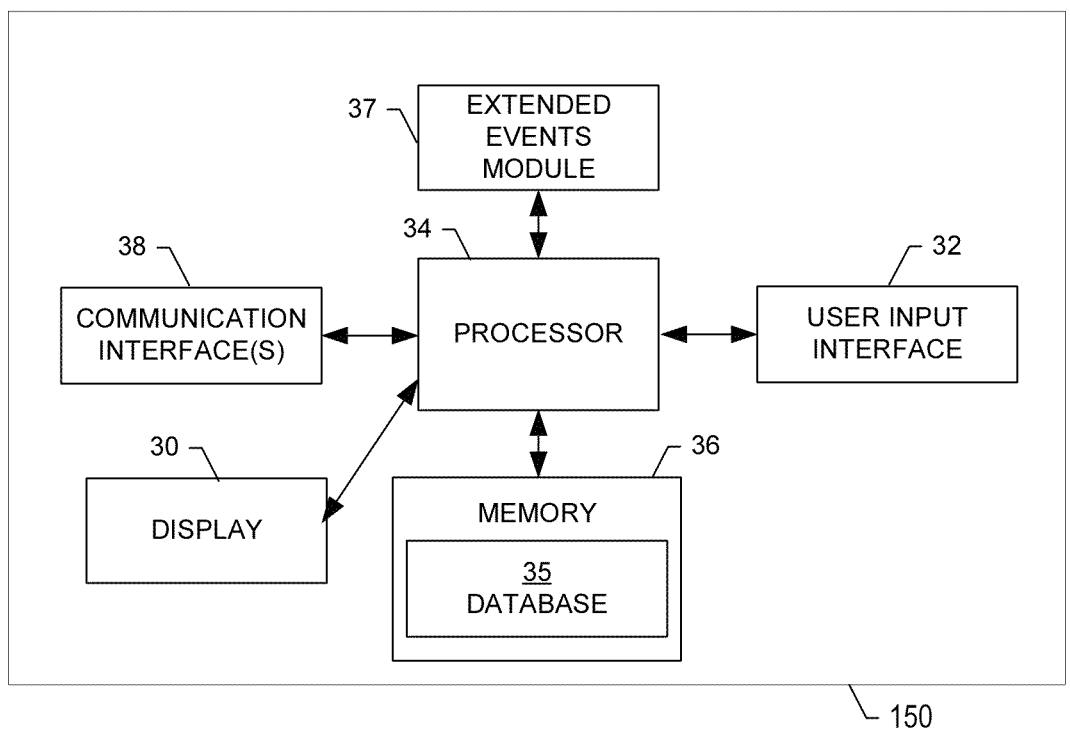
Figure 3:
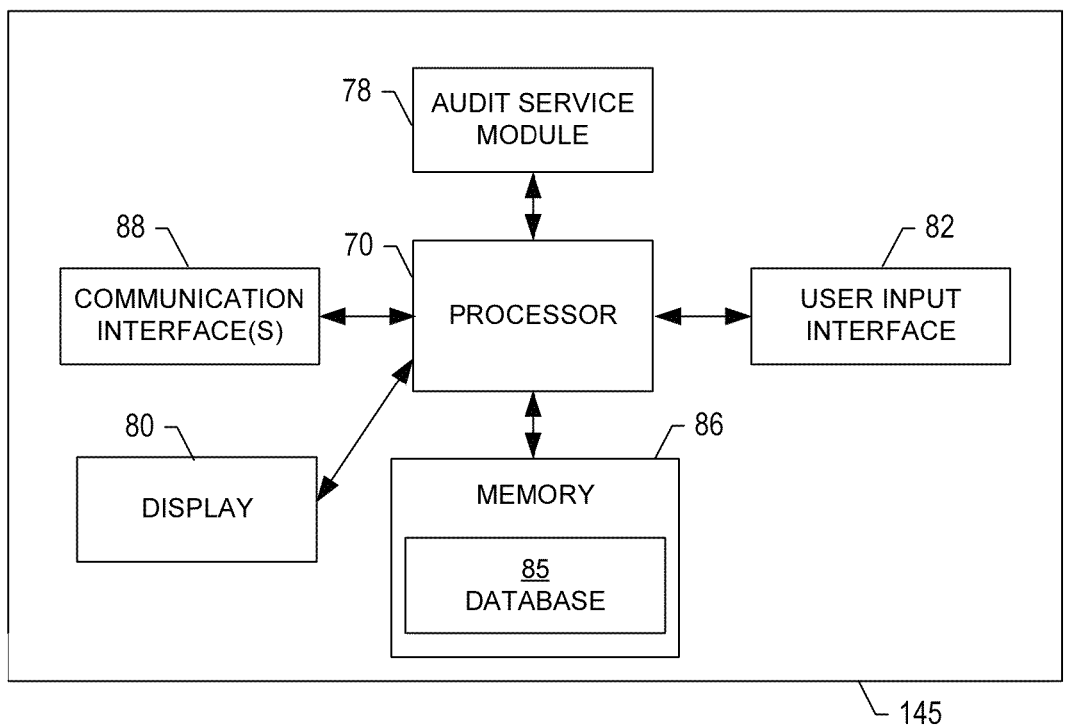
Figure 5:
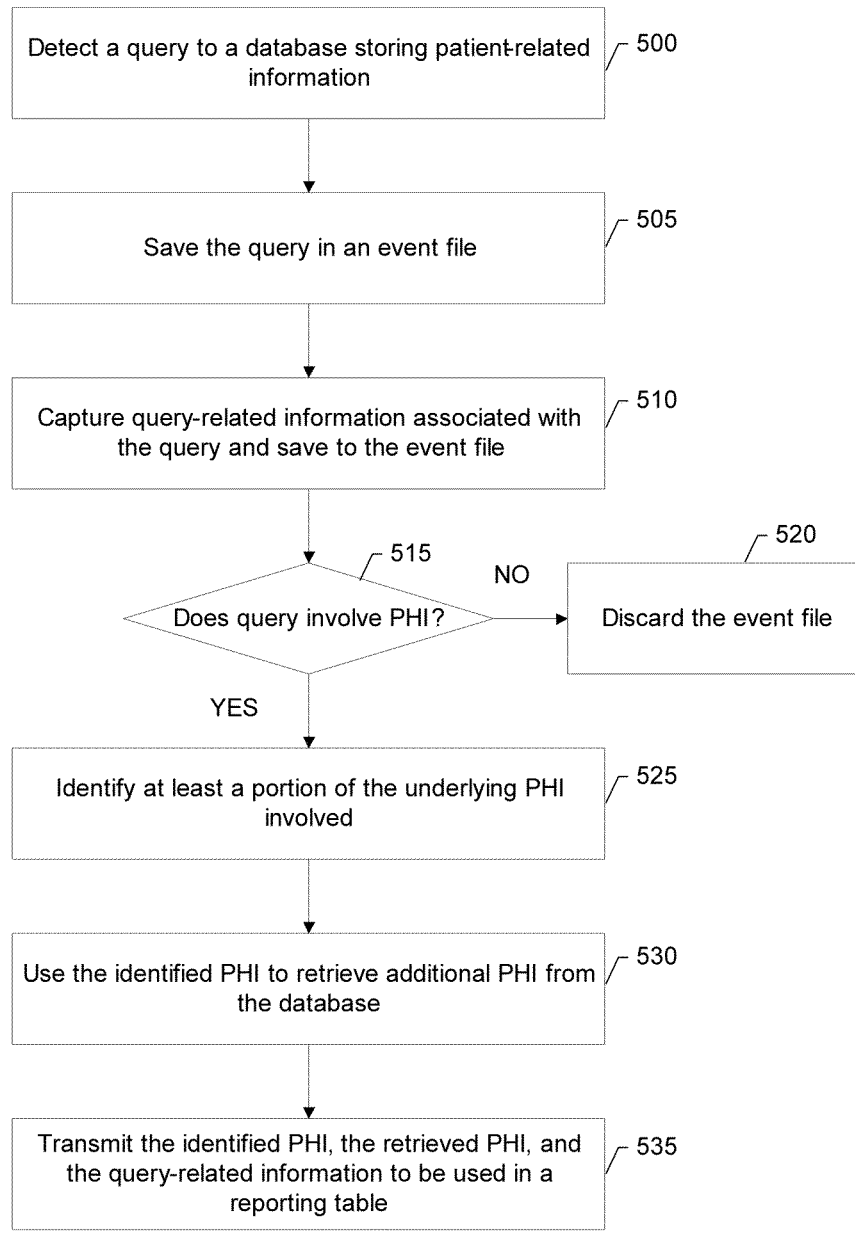

Having thus described the invention in general terms, reference will now be made to the accompanying drawings, which are not necessarily drawn to scale, and wherein:

FIG. 1 is a schematic block diagram of a system according to an exemplary embodiment of the invention;

FIG. 2 is a schematic block diagram of a computing device according to an exemplary embodiment of the invention;

FIG. 3 is a schematic block diagram of a communication device according to an exemplary embodiment of the invention;

FIG. 4 is a diagram illustrating an audit security report according to an exemplary embodiment of the invention; and FIG. 5 is a flowchart of an exemplary method for auditing protected health information according to an exemplary embodiment of the invention.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein. Like reference numerals refer to like elements throughout. As used herein, the terms "data," "content," "information" and similar terms may be used interchangeably to refer to data capable of being transmitted, received and/or stored in accordance with embodiments of the invention. Moreover, the term "exemplary", as used herein, is not provided to convey any qualitative assessment, but instead merely to convey an illustration of an example. Thus, use of any such terms should not be taken to limit the spirit and scope of embodiments of the invention.

As defined herein a "computer-readable storage medium," which refers to a non-transitory, physical or tangible storage medium (e.g., volatile or non-volatile memory device), may be differentiated from a "computer-readable transmission medium," which refers to an electromagnetic signal.

As referred to herein, protected health information refers to any information corresponding to health status, provision of health care, payment for health care or any other suitable information that may be associated with one or more patients. For example, as referred to herein, protected health information may relate to information of one or more patients including, but not limited to: (1) patient names; (2) admission/discharge dates of a patient(s) in a health care facility; (3) address (e.g., home and/or mailing address) information of a patient(s); (4) phone numbers of a patient(s); (5) email addresses of a patient(s); (6) social security numbers of a patient(s); (7) medical record numbers of a patient(s); (8) biographic/demographic information (e.g., date of birth, gender, citizenship, etc.) of a patient(s); (9) medication information of a patient(s); and (10) any other suitable patient specific information.

As used herein, the terms Structured Query Language (SQL) statement(s) or a query statement(s) may be referred to herein interchangeably to denote a programming language used to interact with one or more databases. In an example embodiment, a SQL statement(s) or query statement(s) may allow for the inserting, updating, deleting and/or selecting of data from one or more relational tables stored inside a database(s). Some of the selected data may, but need not, be medical/health care data associated with one or more patients.

General System Architecture

Reference is now made to FIG. 1, which is a block diagram of a system according to exemplary embodiments. As shown in FIG. 1, the system 2 may include one or more electronic devices 100, 105 and 110 (e.g., servers (e.g., SQL servers), workstations, personal computers, laptops, personal digital assistants, smart devices and the like, etc.) which may access one or more network entities such as, for example, a communication device 145 (e.g., a server (e.g., an audit server)), or any other similar network entity, over a network 140, such as a wired local area network (LAN) or a wireless local area network (WLAN), a metropolitan network (MAN) and/or a wide area network (WAN) (e.g., the Internet). In this regard, the communication device 145 is capable of receiving data from and transmitting data to the electronic devices 100, 105 and 110 via network 140. In one exemplary embodiment, the electronic devices 100, 105, 110 may be utilized by clinicians, nurses, pharmacists, physicians, physical therapists, laboratory technicians, and/or any other suitable health care professionals. In an exemplary embodiment, the electronic devices 100, 105, 110 and the communication device 145 may be maintained by a health care institution(s) (e.g., a hospital, a clinic, etc.)

The communication device 145 may communicate with the electronic devices 100, 105, 110. In this regard, the communication device 145 may receive information (e.g., medical information, etc.) from and may transmit information (e.g., medical information) to the electronic devices 100, 105, 110. In one example embodiment, one or more of the electronic devices 100, 105, 110 may send data to the communication device 145 to enable the communication device 145 to determine whether the data includes protected health information for auditing by the communication device 145, as described more fully below.

It should be pointed out that although FIG. 1 shows three electronic devices 100, 105, 110 and one communication device 145, any suitable number of electronic devices 100, 105, 110 and communication devices 145 may be part of the system of FIG. 1 without departing from the spirit and scope of the invention.

Computing Device

Referring now to FIG. 2, a block diagram of a computing device according to an exemplary embodiment is provided. The computing device 150 (e.g., a server (e.g., a SQL server)) is capable of operating as any of electronic devices 100, 105 and 110. In this regard, the electronic devices 100, 105 and 110 may comprise the elements of the computing device of FIG. 2. As shown in FIG. 2, the computing device may include a processor 34 connected to a memory device 36. The memory 36 (also referred to herein as memory device 36) may comprise volatile and/or non-volatile memory, and may store content, information, data or the like. For example, the memory device 36 typically stores content transmitted from, and/or received by, the computing device. Additionally, the memory device 36 may store client applications, software (e.g., software code) algorithms, instructions or the like for the processor 34 to perform steps associated with operation of the computing device.

The memory device 36 may include a database 35 (also referred to herein as an application database 35) (e.g., a relational database) that may store one or more SQL statements. The SQL statements may be captured by the extended events module 37, as described more fully below. Additionally, the memory device 36 may store patient-related information, such as medical information (e.g., medical diagnoses, laboratory results, medications, etc.), patient biographic information, and/or the like that may be accessed by one or more health care applications being used throughout a health care system. Some of the patient-related information may be protected health information associated with patients of a health care institution/facility. The memory device 36 may also store any other suitable information.

The processor 34 may be embodied in a number of different ways. For example, the processor 34 may be embodied as one or more of various hardware processing means such as a coprocessor, a microprocessor, a controller, a digital signal processor (DSP), or various other processing circuitry including integrated circuits such as, for example, an application specific integrated circuit (ASIC). In an example embodiment, the processor 34 may be configured to execute instructions stored in the memory device 36 or otherwise accessible to the processor 34.

The processor 34 may be connected to at least one communication interface 38 or other means for displaying, transmitting and/or receiving data, content, information or the like. In this regard, the communication interface 38 may be capable of connecting to one or more networks. The computing device may also include at least one user interface that may include one or more speakers, a display 30, a user input interface 32, and/or any other suitable devices. For instance, the user input interface 32 may include any of a number of devices allowing the computing device to receive data from a user, such as a keyboard, a keypad, mouse, a microphone, a touch screen display, or any other input device.

The extended events module 37 may be any means such as a device or circuitry operating in accordance with software or otherwise embodied in hardware or a combination of hardware and software (e.g., processor 34 operating under software control, the processor 34 embodied as an ASIC or FPGA specifically configured to perform the operations described herein, or a combination thereof) thereby configuring the device or circuitry to perform the corresponding functions of the processor 34, as described herein. Thus, in examples in which software is employed, a device or circuitry (e.g., the processor 34 in one example) executing the software forms the structure associated with such means.

As described in more detail below, the extended events module 37 may capture and store data based on requests made, for example, by software applications (e.g., health care applications operating within a health care system) to access patient-related information stored in the database 35. In particular, in one example embodiment, the extended events module 37 may capture one or more SQL statements executed by a health care application in order to retrieve information from database 35.

For purposes of illustration and not of limitation, presume that a health care application generates a request to access biographical information of a patient such as, for example, a first name and/or last name of the patient (e.g., a fictional patient named John Doe). The extended events module 37 may detect/capture this request in a query (e.g., a SQL statement(s)) and may determine that the biographical information is in a table(s) of the database 35. As another example, in an instance in which the extended events module 37 detects a request relating to an allergy of a patient, the extended events module 37 may detect/capture this request in a query (e.g., SQL statement(s)) and may determine that a record associated with allergy information of a patient (e.g., John Doe) is included in a table(s) of the database 35. In this regard, the extended events module 37 may monitor and capture one or more queries for information (e.g., medical information) being executed by the software applications of a system (e.g., a health care system) and may identify the information in the database 35.

The extended events module 37 may detect additional information associated with one or more detected queries such as, for example, the user (e.g., a doctor, nurse, etc.) accessing information associated with the queries, the time at which the information was accessed, an application(s) being utilized to access the information, and/or any other suitable information, as described more fully below.

The extended events module 37 may store the captured information associated with one or more queries (e.g., the SQL statement(s)) in a file(s) (e.g., an extended events file(s)) (also referred to herein as an extended events log file(s))). The extended events module 37 may save the file(s) in the memory device 36 and/or a shared memory of another device. Additionally, in an example embodiment, the extended events module 37 may provide the file(s) to the communication device 145 (also referred to herein as audit device 145). The communication device 145 may save the file(s) in a memory (e.g., memory 86).

In one example embodiment, the extended events module 37 may periodically generate files including the captured queries (e.g., the SQL statements) and additional information. For instance, the extended events module 37 may generate a new file(s) with captured queries and additional information periodically during predetermined time periods (e.g., every twenty minutes, etc.). In this manner, the communication device 145 may receive the completed files from the extended events module 37 while the extended events module 37 writes captured queries and additional data to a new file. The communication device 145 may analyze the file(s) received from the extended events module 37 to determine whether the files include protected health information, as described more fully below.

Communication Device

FIG. 3 illustrates a block diagram of a communication device according to an exemplary embodiment of the invention. The communication device 145 may, but need not, be a network entity such as, for example, a server (e.g., an audit server). The communication device 145 includes various means for performing one or more functions in accordance with exemplary embodiments of the invention, including those more particularly shown and described herein. It should be understood, however, that one or more of the communication devices may include alternative means for performing one or more like functions, without departing from the spirit and scope of the invention. More particularly, for example, as shown in FIG. 3, the communication device 145 may include a processor 70 connected to a memory 86 (also referred to herein as memory device 86). The memory 86 may comprise volatile and/or non-volatile memory, and typically stores content (e.g., media content), data, information or the like.

For example, the memory 86 may store content transmitted from, and/or received by, the electronic devices 100, 105 and 110. In this regard, in an exemplary embodiment, the memory 86 may store data received from various disparate sources. For example, the memory 86 may store one or more files (e.g., extended events files) received by the communication device 145 from one or more of the electronic devices 100, 105, 110 (e.g., computing devices 150). In an example embodiment, the file(s) (e.g., an extended events file(s)) received from one or more electronic devices 100, 105, 110 may be stored in a secure shared directory of the memory 86. The memory 86 may store medical information. Some of the medical information may be received from one or more of the electronic devices 100, 105, 110. The medical information may, but need not, include protected health information of one or more patients.

Also for example, the memory 86 typically stores client applications, instructions, algorithms or the like for execution by the processor 70 to perform steps associated with operation of the communication device 145 in accordance with embodiments of the invention. As explained below, for example, the memory 86 may store one or more client applications such as for example software (e.g., software code also referred to herein as computer code).

The memory 86 may include a database 85 (also referred to herein as audit database 85). The audit database may include one or more items of metadata (e.g., predefined metadata)

specifying medical information that qualifies as protected health information. The metadata may be configurable and may be adjusted, by the audit service module 78, to exclude some items of medical information as PHI and/or include additional items of medical information as PHI. The database 85 may include a staging table (also referred to herein as a staging directory), a reporting table and any other suitable table(s). For example, in one example embodiment the metadata specifying the medical information that qualifies as PHI may be designated in one or more tables (e.g., a metadata table).

The processor 70 may be embodied in a variety of ways. For instance, the processor 70 may be embodied as a controller, coprocessor microprocessor of other processing devices including integrated circuits such as, for example, an application specific integrated circuit (ASIC), a field programmable gate array (FPGA). In an exemplary embodiment, the processor 70 may execute instructions stored in the memory 86 or otherwise accessible to the processor 70.

The communication device 145 may include one or more logic elements for performing various functions of one or more client applications. In an exemplary embodiment, the communication device 145 may execute the client applications. The logic elements performing the functions of one or more client applications may be embodied in an integrated circuit assembly including one or more integrated circuits (e.g., an ASIC, FPGA or the like) integral or otherwise in communication with a respective network entity (e.g., computing system, client, server, etc.) or more particularly, for example, a processor 70 of the respective network entity.

In addition to the memory 86, the processor 70 may also be connected to at least one interface or other means for displaying, transmitting and/or receiving data, content or the like. The interface(s) may include at least one communication interface 88 or other means for transmitting and/or receiving data, content or the like. In this regard, the communication interface 88 may include, for example, an antenna and supporting hardware and/or software for enabling communications with a wireless communication network. For example, the communication interface(s) may include a first communication interface for connecting to a first network, and a second communication interface for connecting to a second network. In this regard, the communication device is capable of communicating with other devices such as, for example, electronic devices 100, 105 and 110 over one or more networks (e.g., network 140) such as a Local Area Network (LAN), wireless LAN (WLAN), Wide Area Network (WAN), Wireless Wide Area Network (WWAN), the Internet, or the like. Alternatively, the communication interface may support a wired connection with the respective network.

In addition to the communication interface(s), the interface(s) may also include at least one user interface that may include one or more earphones and/or speakers, a display 80, and/or a user input interface 82. The user input interface, in turn, may comprise any of a number of devices allowing the entity to receive data from a user, such as a microphone, a keypad, keyboard, a touch display, a joystick, image capture device, pointing device (e.g., mouse), stylus or other input device.

In an exemplary embodiment, the processor 70 may be in communication with and may otherwise control an audit service module 78. The audit service module 78 may be any means such as a device or circuitry operating in accordance with software or otherwise embodied in hardware or a combination of hardware and software thereby configuring the device or circuitry (e.g., a processor, controller, microprocessor or the like) to perform the corresponding functions of the audit service module 78, as described below. In examples in which software is employed, a device or circuitry (e.g., processor 70 in one example) executing the software forms the structure associated with such means. As such, for example, the audit service module 78 may be configured to, among other things, access the file(s) (e.g., the extended event files) in the shared directory of the memory 86 and move the file(s) in the shared directory to a staging table of the database 85 for further processing by the audit service module 78 and/or processor 70.

In this regard, the audit service module 78 may parse and analyze the data such as, for example, queries (e.g., SQL statements) in the staging table corresponding to the file(s) (e.g., an extended events file) to determine whether the data includes protected health information. Additionally or alternatively, the audit service module 78 and/or processor 70 may execute the queries to retrieve information from the database (e.g., database 35) corresponding to the queries. The audit service module 78 may determine whether data of the queries and/or the retrieved information from the database (e.g., database 35) includes one or more items of protected health information by comparing the data being analyzed to metadata (e.g., patient name information, patient biographic information, medication information, patient social security number, etc.) specifying medical information qualifying as protected health information.

In an instance in which the audit service module 78 detects that the data (e.g., a SQL statement(s)) of the file(s) in the staging table corresponds to PHI, the audit service module 78 may designate the data as corresponding to PHI. On the other hand, in an instance in which the audit service module 78 determines that an item of data in the staging table being analyzed does not correspond to PHI, the audit service module 78 may discard the data.

The audit service module 78 may continue to parse and analyze each of the items of data in the file(s) of the staging table to determine whether the data corresponds to PHI. Each item of data identified by the audit service module 78 as corresponding to PHI based in part on analyzing the information of the metadata table may be designated by the audit service module 78 as PHI and may be saved in the database 85. Additionally, each item of data of the file(s) in the staging table that is not detected as matching or corresponding to information in the metadata table may be designated by the audit service module 78 as non-PHI data and may be discarded.

The audit service module 78 may transfer the data designated as protected health information to a reporting table of the audit database 85. The audit service module 78 may utilize the protected health information to generate one or more audit reports, as described more fully below. An audit report(s) may be generated by the audit service module 78 in response to receipt of a request from a device(s) (e.g., one or more of electronic device 100, 105, 110). For instance, a user may utilize a device to send a request to the communication device 145 for an audit report.

The audit report may include, for example, information indicating an application (e.g., a health care application) that generated a query (e.g., a query statement or SQL statement) for the protected health information (e.g., demographic information), the identity of a user (e.g., a nurse, a physician, etc.) accessing the protected health information, the time in which the protected health information was accessed and other suitable data.

Exemplary System Operation

Exemplary embodiments of the invention may provide an efficient and reliable mechanism for monitoring/auditing protected health information of one or more patients in a health care system.

In this regard, an exemplary embodiment may enable an electronic device(s) (e.g., an SQL server) to capture one or more SQL statements executed against a database storing patient-related information, including protected health information. These SQL statements may be generated by software applications (e.g., health care applications) of health care system, or by any party, seeking to access the patient-related information stored in the database. The extended events module may include the queries (e.g., SQL statements) in a file(s) (e.g., an extended events file) that may be provided to a communication device 145 (e.g., an audit device). In an example embodiment, the extended events module 37 may detect data of one or more captured queries and may determine that the detected data is associated with an application that does not generate protected health information. In this regard, the extended events module 37 may not include the detected data in the file(s) to be sent to the communication device 145 since the extended events module 37 determined that the detected data does not correspond to protected health information.

The communication device may store the file(s) in a shared directory of a memory. In order to process the data such as, for example, queries (e.g., SQL statements) of the file(s), an audit service module may transfer the file(s) from a shared directory to a staging table. The audit service module may parse and analyze the queries of the file(s) to determine whether the data of the queries includes protected health information. Additionally or alternatively, the audit service module 78 and/or processor 70 may execute the queries to retrieve information from the database (e.g., database 35). The audit service module 78 may determine whether the data of the queries and/or the retrieved information from the database (e.g., database 35) includes protected health information by comparing the data and the retrieved information to metadata specifying information that qualifies as protected health information. The analyzed data that is determined by the audit service module to correspond to the metadata may be designated as protected health information and may be provided to a reporting table. The audit service module may utilize the protected health information in the reporting table along with other captured information to generate one or more audit reports, as described more fully below.

As an example in which protected health information may be detected and audited consider the following. In an example embodiment, an extended events module 37 of a computing device may capture one or more SQL statements (also referred to herein as queries) executed against a database storing patient-related information. These SQL statements, or queries, may be associated with events being executed by one or more software applications (e.g., health care applications) of a health care facility (e.g., a hospital, clinic, etc.).

The SQL statements may relate to one or more tasks or actions performed by the software applications of the health care system. The tasks or actions may relate to health care tasks or any other tasks/or actions (e.g., non-health care tasks/actions) of the software applications.

For purposes of illustration and not of limitation, one or more SQL statement(s) may, but need not, be captured, by the extended events module 37 in response to actions that software applications may perform in relation to patients of a health care facility (e.g., a hospital, a clinic, etc.) including but not limited to scheduling an appointment or patient visit, admitting or discharging a patient(s) to the health care facility, assigning a patient to a room, accessing electronic medical records of a patient(s), medication information of a patient(s) or any other medical information of a patient. In an instance in which the extended events module 37 generates an SQL statement in response to an action/task being performed by a software application, the extended events module 37 may access information (e.g., an electronic medical record(s), medication information, etc.) in a database 35 of a memory 36.

In an example embodiment, some of the SQL statements may be captured by the extended events module 37 in response to receipt of one or more queries for information by one or more of the software applications of the health care system. As an example, the one or more queries may relate to one or requests for patient data including, but not limited to, information relating to a medication and/or medical record of a patient, or any other suitable information. The queries may be initiated in response to requests by a user (e.g., a nurse, a physician, a lab technician, etc.) utilizing a device (e.g., electronic device 100) for access to patient data or any other suitable data.

Additionally, in an instance in which the extended events module 37 captured an SQL statement(s), the extended events module 37 may also detect/capture additional information associated with a corresponding task/action implemented by an application(s). For instance, the extended events module 37 may detect/capture: (1) the action (e.g., the type of action) that was performed; (2) an item(s) of data (e.g., a medical record or patient data record) that was viewed or accessed; (3) the identity of an individual viewing or accessing an item(s) of data; (4) the date and time that an item(s) of data was accessed; (5) whether an item(s) of data was modified or updated by an individual; (6) whether an item(s) of data was deleted by an individual; (7) the identity of an application (e.g., a health care application) in which an item(s) of data was accessed; and (8) any other suitable information. This detected/captured additional information may be utilized to generate one or more audit reports, as described more fully below.

The extended events module 37 may include the generated SQL statements and the additional detected/captured information in a file(s) (e.g., an extended event file(s)). The extended events module 37 may periodically (e.g., every twenty minutes) generate a new file(s) that includes SQL statements and additional detected/captured information. The file(s) may be stored in a memory 36 of the computing device 150. Additionally, upon the completion of each newly generated file(s), the extended events module 37 and/or the processor 34 may send the file(s) to the audit device 145. In this regard, the audit service module 78 may store the received file(s) in a memory 86. In an example embodiment, the audit service module 78 may store the received file(s) in a shared directory (e.g., a secure shared directory) of the memory 86.

To process the file(s), the audit service module 78 may move the file(s) from the shared directory of the memory 86 to a staging table of an audit database 85. In this manner, the audit service module 78 may compare the information of each of the SQL statements to metadata designating information that qualifies as protected health information. In an example embodiment, the metadata may be included in a metadata table stored in the database 85 of the memory 86. In an instance in which the audit service module 78 determines that the information associated with a corresponding SQL statement(s) matches or corresponds to an item(s) of information (e.g., a patient name, a patient date of birth, etc.) in the metadata, the audit service module 78 may determine that the information associated with the SQL statement(s) includes protected health information. On the other hand, in an instance in which the audit service module 78 determines that the information associated with the SQL statement(s) does not match or correspond to an item(s) of information in the metadata, the audit service module 78 may determine that the information associated with the SQL statement does not include protected health information. In other words, the audit service module 78 may determine that this information corresponds to non-PHI data. In this regard, the audit service module 78 may discard the non-PHI data.

The audit service module 78 may include move the detected protected health information associated with SQL statement and corresponding detected/captured additional information (e.g., an identity of a user accessing the PHI, the identity of the application corresponding to the PHI, etc.) to a reporting table which may be stored in the audit database 85. In this manner, the audit service module 78 may utilize one or more items of the protected health information and the additional information to generate one or more audit reports In one example embodiment, in an instance in which the audit service module 78 generates an audit report(s), the audit service module 78 may retrieve one or more values and fields associated (e.g., name fields, etc.) with the PHI data and may utilize these values and fields to obtain additional patient health information that may also be included in the audit report(s).

Referring now to FIG. 4, a diagram illustrating an audit report according to an example embodiment is provided. The audit report 3 may be generated by the audit service module 78. In the example embodiment of FIG. 4, the audit service module 78 may generate the audit report 3 based in part on analyzing one or more items of protected health information and associated data that was captured/detected along with one or more corresponding SQL statements. The protected health information and the associated data analyzed by the audit service module 78 may be stored in the reporting table of the audit database 85.

The audit report 3 may include one or more fields such as, for example, date accessed, medical record (Med Rec), visit identifier (Id), patient name information, a user login identifier, a user name, workstation, application/program, action, and data. One or more of these fields may be required by the ARRA for inclusion in an audit report. In the audit report 3, the patient name associated with the patient name field may correspond to a fictitious person (e.g., Kennedy Pearson) for purposes of illustration and not of limitation. Additionally, the user name information associated with the user name field may correspond to a fictitious person (e.g., Patrick Robinson) for purposes of illustration and not of limitation. In this example embodiment, the user (e.g., Kennedy Pearson) may be a clinician (e.g., a nurse, a laboratory technician, etc.) of a health care facility (e.g., a hospital, a clinic, etc.). The audit service module 78 may include data indicating one or more workstations associated with the workstation field that was utilized by a user to access or create an item(s) of protected health information (e.g., demographic information) of a patient.

The audit service module 78 may also include information in the audit report 3 indicating the application (e.g., a clinical CareStation application) that was being executed in an instance in which a corresponding action (e.g., access, creation of medical information) was performed.

In an example embodiment, the audit service module 78 may generate the audit report 3 in response to receipt of a request from a device (e.g., electronic device 105). For instance, the device (e.g., electronic device 105) may send a request to the audit device 145 requesting receipt of an audit report in response to receipt of a selection by a user (e.g., a nurse, physician, etc.). In response to receipt of the request, the audit service module 78 may generate the audit report and may send the generated audit report to the requesting device.

Referring now to FIG. 5, an exemplary method for auditing protected health information of one or more patients is provided. At operation 500, an apparatus (e.g., an audit device 145) may detect a query to a database (e.g., database 35) storing patient-related information. At operation 505, an apparatus (e.g., audit device 145) may save the query in an event file. At operation 510, an apparatus (e.g., audit device 145) may capture query related-information associated with the query and save the query related-information to the event file. At operation 515, an apparatus (e.g., audit device 145) may determine whether the query involves PHI.

At operation 520, an apparatus (e.g., audit device 145) may discard the event file in response to determining that the query does not involve PHI. At operation 525, an apparatus (e.g., audit device 145) may identify at least a portion of underlying PHI involved. At operation 530, an apparatus (e.g., audit device 145) may use the identified PHI to retrieve additional PHI from the database. At operation 535, an apparatus (e.g., audit device 145) may transmit the identified PHI, the retrieved PHI and the query-related information to be used in a reporting table.

It should be pointed out that FIG. 5 is a flowchart of a system, method and computer program product according to exemplary embodiments of the invention. It will be understood that each block or step of the flowchart, and combinations of blocks in the flowchart, can be implemented by various means, such as hardware, firmware, and/or a computer program product including one or more computer program instructions. For example, one or more of the procedures described above may be embodied by computer program instructions. In this regard, in an example embodiment, the computer program instructions which embody the procedures described above are stored by a memory device (e.g., memory 86, memory 36) and executed by a processor (e.g., processor 70, processor 34, extended events module 37, audit service module 78). As will be appreciated, any such computer program instructions may be loaded onto a computer or other programmable apparatus (e.g., hardware) to produce a machine, such that the instructions which execute on the computer or other programmable apparatus cause the functions specified in the flowchart blocks or steps to be implemented. In some embodiments, the computer program instructions are stored in a computer-readable memory that can direct a computer or other programmable apparatus to function in a particular manner, such that the instructions stored in the computer-readable memory produce an article of manufacture including instructions which implement the function specified in the flowchart blocks or steps. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart blocks or steps.

Accordingly, blocks or steps of the flowchart support combinations of means for performing the specified functions and combinations of steps for performing the specified functions. It will also be understood that one or more blocks or steps of the flowchart, and combinations of blocks or steps in the flowchart, can be implemented by special purpose hardware-based computer systems which perform the specified functions or steps, or combinations of special purpose hardware and computer instructions.

In an exemplary embodiment, an apparatus for performing the methods of FIG. 5 above may comprise a processor (e.g., the processor 70, the processor 34, the extended events module 37, the audit service module 78) configured to perform some or each of the operations described above. The processor may, for example, be configured to perform the operations by performing hardware implemented logical functions, executing stored instructions, or executing algorithms for performing each of the operations. Alternatively, the apparatus may comprise means for performing each of the operations described above. In this regard, according to an example embodiment, examples of means for performing operations may comprise, for example, the processor 34, the processor 70 (e.g., as means for performing any of the operations described above), the extended events module 37, the audit service module 78 and/or a device or circuit for executing instructions or executing an algorithm for processing information as described above.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   detecting a query to access information stored in a database comprising patient-related information;
   saving the query in an event file;
   capturing query-related information associated with the query and saving the query-related information in the event file;
   determining, via a processor, whether data of the query itself comprises protected health information;
   executing the query;
   determining whether data returned from executing the query comprises protected health information;
   determining whether a software application that generated the query has access to protected health information;
   wherein the query is determined to comprise protected health information in an instance in which it is determined that either the query itself or the data returned by the query comprises protected health information;
   wherein the query is determined not to comprise protected health information in an instance in which it is determined that the software application does not have access to protected health information; and
   transmitting, in response to determining that the query comprises protected health information, the query-related information to be used in a reporting table.

2. The method of claim 1 further comprising:
   identifying at least a portion of the underlying protected health information involved in the query; and
   transmitting the identified protected health information to be used in the reporting table.

3. The method of claim 2, further comprising:
   using the identified protected health information to retrieve additional protected health information to be used in the reporting table.

4. The method of claim 1 further comprising:
   determining that the query does not involve protected health information; and
   discarding the event file.

5. The method of claim 1, wherein the query comprises a Structured Query Language (SQL) statement generated by a health care application operating within a health care system.

6. The method of claim 1, wherein the query-related information comprises the identity of a health care application generating the query, the identity of a user operating the health care application, a time at which the health care application generated the query, a workstation used to access the health care application, or a combination thereof.

7. The method of claim 1, wherein determining that the query involves protected health information further comprises determining that the query involves protected health information by comparing the query-related information to metadata designating medical information qualifying as protected health information.

8. The method of claim 7, wherein determining that the query includes protected health information further comprises comparing content of the query and the information to which access is requested to one or more items of metadata specifying information designated as protected health information.

9. The method of claim 7, wherein determining that the information to which access is requested by the query comprises protected health information further comprises:
   executing the query; and
   determining that a result of the executed query comprises protected health information.

10. An apparatus comprising:
    at least one memory; and
    at least one processor configured to cause the apparatus to:
       detect a query to access information stored in a database comprising patient-related information;
       save the query in an event file;
       capture query-related information associated with the query and save the query-related information in the event file;
       determine whether data of the query itself comprises protected health information;
       execute the query;
       determine whether data returned from executing the query comprises protected health information,
       determine whether a software application that generated the query has access to protected health information;
       wherein the query is determined to comprise protected health information in an instance in which it is determined that either the query itself or the data returned by the query comprises protected health information;
       wherein the query is determined not to comprise protected health information in an instance in which it is determined that the software application does not have access to protected health information; and transmit, in response to determining that the query involves protected health information, the query-related information to be used in a reporting table.

11. The apparatus of claim 10, wherein the processor is further configured to cause the apparatus to:
identify at least a portion of the underlying protected health information involved in the query; and
transmit the identified protected health information to be used in the reporting table.

12. The apparatus of claim 11, wherein the processor is further configured to cause the apparatus to:
use the identified protected health information to retrieve additional protected health information to be used in the reporting table.

13. The apparatus of claim 10, wherein the processor is further configured to cause the apparatus to:
determine that the query does not involve protected health information; and
discard the event file.

14. The apparatus of claim 10, wherein the query comprises a Structured Query Language (SQL) statement generated by a health care application operating within a health care system.

15. The apparatus of claim 10, wherein the query-related information comprises the identity of a health care application generating the query, the identity of a user operating the health care application, a time at which the health care application generated the query, a workstation used to access the health care application, or a combination thereof.

16. The apparatus of claim 10, wherein the processor is further configured to cause the apparatus to:
determine that the query involves protected health information by comparing the query-related information to metadata designating medical information qualifying as protected health information.

17. The apparatus of claim 16, wherein determining that the query includes protected health information further comprises comparing content of the query and the information to which access is requested to one or more items of metadata specifying information designated as protected health information.

18. The apparatus of claim 16, wherein the processor is further configured to cause the apparatus to:
determine that the information to which access is requested by the query comprises protected health information by:
executing the query; and
determining that a result of the executed query comprises protected health information.

19. A computer program product comprising at least one non-transitory computer-readable storage medium having computer-executable program code instructions stored therein, the computer executable program code instructions comprising:
program code instructions configured to detect a query to access information stored in a database comprising patient-related information;
program code instructions configured to save the query in an event file;
program code instructions configured to capture query-related information associated with the query and save the query-related information in the event file;
program code instructions configured to determine whether data of the query itself comprises protected health information;
program code instructions configured to execute the query;
program code instructions configured to determine whether data returned from executing the query comprises protected health information,
program code instructions configured to determine whether a software application that generated the query has access to protected health information;
wherein the query is determined to comprise protected health information in an instance in which it is determined that either the query itself or the data returned by the query comprises protected health information;
wherein the query is determined not to comprise protected health information in an instance in which it is determined that the software application does not have access to protected health information; and
program code instructions configured to cause transmission, in response to determining that the query involves protected health information, of the query-related information to be used in a reporting table.

20. The computer program product of claim 19, further comprising:
program code instructions configured to identify at least a portion of the underlying protected health information involved in the query; and
program code instructions configured to cause transmission of the identified protected health information to be used in the reporting table.

* * * * *